US007910369B2

(12) United States Patent
West et al.

(10) Patent No.: US 7,910,369 B2
(45) Date of Patent: Mar. 22, 2011

(54) CULTURE SYSTEMS FOR EX VIVO DEVELOPMENT

(75) Inventors: Michael D. West, Mill Valley, CA (US); Karen B. Chapman, Mill Valley, CA (US); Irina V. Klimanskaya, Upton, MA (US)

(73) Assignee: Advanced Cell Technology, Inc., Santa Monica, CA (US)

( * ) Notice: Subject to any disclaimer, the term of this patent is extended or adjusted under 35 U.S.C. 154(b) by 647 days.

(21) Appl. No.: 11/211,174

(22) Filed: Aug. 24, 2005

(65) Prior Publication Data

US 2006/0031955 A1 Feb. 9, 2006

Related U.S. Application Data

(63) Continuation of application No. 11/028,345, filed on Jan. 3, 2005, now abandoned.

(60) Provisional application No. 60/539,796, filed on Jan. 28, 2004, provisional application No. 60/534,447, filed on Jan. 2, 2004.

(51) Int. Cl.
  C12N 5/00 (2006.01)
  C12N 5/02 (2006.01)
  C12N 5/071 (2006.01)
  C12N 5/07 (2006.01)
  C12N 5/10 (2006.01)
(52) U.S. Cl. .................. 435/373; 435/366; 435/349
(58) Field of Classification Search .................. 435/325, 435/373, 377, 366, 349
  See application file for complete search history.

(56) References Cited

U.S. PATENT DOCUMENTS 5,340,740 A  8/1994 Petitte et al.

FOREIGN PATENT DOCUMENTS
WO  WO03/048344  6/2003

OTHER PUBLICATIONS

Thomson. PNAS, 92:7844-7848, Aug. 1995.*
Lim et al. Proteomics, 2:1187-1203(2002).*
Prowse et al. Proteomics, 5: 978-989, 2005.*
Xu. Nat. Biotech., 19:971-974, 2001.*
Richards et al. Stem Cells, 21:546-556, 2003.*
Xenotransplantation: Science, Ethics, and Public Policy, National Academy Press, Washington DC, 1996, p. 50.*
Yang. Poultry Science, 73: 965-975, 1994.*
http://cancerweb.ncl.ac.uk/cgi-bin/omd?specific+pathogen-free+organisms,definition of "specific pathogen-free organisms", accessed online Oct. 1, 2007, publicly availabled Dec. 12, 1998.*
Lim et al. Proteomics, 2:1187-1203, 2002.*
Thomson. PNAS, 92: 7844-7848, Aug. 1995.*
Amit et al., (2000) "Clonally Derived Human Embryonic Stem Cell Lines Maintain Pluripotency and Proliferative Potential for Prolonged Periods of Culture," *Developmental Biology*, 227:271-278.
Thomson et al., (1998) "Embryonic Stem Cell Lines Dervied from Human Blastocysts," *Science*, 282:1145-1147.
Verfaillie et al., (2002) "Stem Cells: Hype and Reality," Hematology, 369-391.
Avian Embryo. http://www.msstate.edu/dept/poultry/avianemb.htm#stages, retrieved online Sep. 20, 2006.
"Ostrich," http://en.wikipedia.org/w/index.php?title=Ostrich&printable=yes, retrieved online, Sep. 20, 2006.
"The Placental Mammal and Reproduction." http://www.earthlife.net/mammals/reproduction.html, retrieved online Sep. 20, 2006.
Fontaine-Perus et al., 1995, Mouse-chick chimera: a new model to study the in ovo developmental potentialities of mammalian somites, Development 121:1705-1718.
Fontaine-Perus et al., 1997, Mouse-chick chimera: a developmental model of murine neurogenic cells, Development 124:3025-3036.
Gray, Gray's Anatomy, Anatomy of the Human Body, Philadelphia: Lea & Febiger, 1918: Bartleby.com 2000, www.bartleby.com/107/. [Sep. 20, 2006], Chapter 2.
Guidelines for Human Embryonic Stem Cell Research by the National Research Council and Institute of Medicine of the National Academies; The National Academies Press, Washington, D.C., 2005, pp. 119-120.
Paulescu et al., 2005. Variation in Macrophage-Migration-Inhibitory-Factor Immunoreactivity During Porcine Gestation. Biol. of Reprod. 72:949-953.
Stojkovic et al., 2004, Derivation, growth and applications of human embryonic stem cells, Reproduction 128:259-267.
Sylvester et al., 2004. Stem Cells, Arch. Surg. 139:93-99.
Dorland's Illustrated Medical Dictionary, 2007, (URL: http://www.mercksource.com/pp/us/cns/cns_hl_dorlands.jspzQzpgzEzzSzppdocszSzuszSzcommonzSzdorlandszSzdorlandzSzdmd_e_18zPzhtm>.
Enclyclopaedia Britannica Artcle, 2007, "Yolk" (URL: http://search.eb.com/eb/article-9077997> (retrieved Jan. 11, 2007)).
Goldstein et al., 2002, Integration and Differentiation of Human Embryonic Stem Cells Transplanted to the Chick Embryo, Dev. Dynamics 225:80-886.

* cited by examiner

*Primary Examiner* — Thaian N Ton
(74) *Attorney, Agent, or Firm* — David C. Scherer; Bozicevic, Field & Francis LLP

(57) ABSTRACT

The present invention provides methods for the culture of animal pluripotent stem cells and their differentiated progeny cells, tissues, and organs, and nonhuman animal embryos and fetuses.

14 Claims, 6 Drawing Sheets

CULTURE SYSTEMS FOR EX VIVO DEVELOPMENT

CROSS REFERENCE TO RELATED APPLICATIONS

This application is a continuation of U.S. application Ser. No. 11/028,345, filed Jan. 3, 2005, now abandoned which claims the benefit under 35 U.S.C. §119(e) of U.S. Provisional Application Ser. No. 60/534,447, filed Jan. 2, 2004 and U.S. Provisional Application Ser. No. 60/539,796, filed Jan. 28, 2004, the entire disclosures of which are hereby incorporated by reference.

FIELD OF THE INVENTION

This invention generally relates to cells, tissue, and organ culture technology. More particularly, the invention relates to methods for culturing and differentiating animal pluripotent stem cells and non-human mammalian embryos and fetuses.

BACKGROUND OF THE INVENTION

Advances in nuclear transfer and embryonic stem cell technology have facilitated the cloning of non-human animals for diverse applications including agriculture, xenotransplantation, disease models, recombinant protein production, and novel means of manufacturing human cells for use in medical therapies, diagnosis, and discovery research. Each of these practical applications would benefit from new technologies to improve efficiencies in the production of animals, tissues, and cells. In the case of animal cloning, the high cost of recipient females to gestate the cloned fetuses often makes the commercialization of cloned animals impractical. In the case of the therapeutic uses of pluripotent stem cells, many pluripotent cells such as human embryonic stem (hES) cells, are problematic to culture using traditional cell culture technology. The cells are dependent on a close association with similar undifferentiated cells and often require being cultured in juxtaposition with embryonic fibroblast feeder cells in order to maintain them in the undifferentiated state.

In addition, while some cells such as hES cells have a demonstrated potential to differentiate into any and all of the cell types in the human body including complex tissues, and while genes expressed uniquely in many differentiated cell types are known allowing genetic selection and purification of populations of any cell type of interest, nevertheless, there is need for new technologies to influence the differentiation of pluripotent stem cells such as hES cells, new means of allowing the cells to differentiate in a three dimensional tissue culture environment, and novel means of purifying the target cells of interest, and techniques such as these that can be performed in SPF conditions to minimize the risk of pathogen transmission into humans.

In the field of the cultivation of human cells for human cell therapy, regulatory agencies require production methods wherein the cells are grown in defined conditions with stringent control over contact of the cells (or anything that may come in contact with the cells) with uncharacterized materials that are a potential source of pathogens. In the case of human embryonic stem (hES) cells, it is desirable to identify a means of cultivating the cells in pathogen-free conditions, differentiating downstream progeny of the cells, scale up the number of the cells for batch production, cryopreservation, and genetic modification.

The original culture of hES cells as reported by Thomson et al (Science. 1998 Nov. 6; 282(5391):1145-7) was accomplished by culturing the inner cell mass of human blastocysts in co-culture with feeder layer of embryonic murine fibroblasts under culture conditions well known in the art of tissue culture to generate ES cell lines. The murine fibroblasts provide largely uncharacterized factors that promote the growth of ES cells while maintaining them in an undifferentiated state. However, the embryonic murine fibroblasts are also a potential source of pathogens including uncharacterized retroviruses. Therefore, novel means of isolating, culturing, and differentiating hES cells and other cells are of great practical value. While avian CEFs have been shown to support the growth of murine ES cells (Yang & Petitte, 1994), and the use of avian cytokines has been described in in non-human mammalian embryonic stem cell culture, (*Poultry Science* 73: 965-974), there has been no description of the possibility that avian CEFs could be useful in providing SPF support for the growth of other mammalian ES cells such as hES cells.

In addition, because of the innate capacity of hES cells to organize into complex three dimensional tissues including organogenesis, and because the growth of tissues in culture systems beyond the size of approximately 0.5 mm in thickness is impractical without a means of supplying vascular support, there is a need for developing conditions that allow for the growth of solid tissues and conditions that provide suitable vascular support for such growing tissue with a dimensions of greater than 0.5 mm while maintaining the cells in a specific pathogen-free environment.

The avian egg is a relatively well-characterized structure that has evolved as a means of providing physiological support to a developing vertebrate embryo, including nutritional support, waste disposal, and gas exchange. The ovum of avian species such as the domestic chicken (*Gallus domesticus*) is that part of the egg commonly called the "yolk" (FIG. 1). The bulk of the ovum is a colloidal suspension of nutrients while a small volume of cytoplasm is concentrated in a region approximately 3 mm in diameter called the blastodisc on the animal pole. Following fertilization, the ovum traverses the oviduct acquiring albuminous material (egg white) and finally the shell membrane and the calcified egg shell.

In the case of an egg that has become fertilized by sperm subsequent to ovulation and prior to encapsulation into the shell, the blastodisc will undergo repeated rounds of karyokinesis and cytokinesis until at about the time the egg is laid, a collection of cells called the blastoderm has formed that is roughly equivalent to the stage of mammalian embryos at the blastocyst stage. Therefore, cultured avian blastodermal cells are occasionally referred to as avian embryonic stem cells (aES cells) and those from species of domestic chicken are referred to as chicken embryonic stem (cES) cells (U.S. Pat. No. 5,340,740). Following the formation of primitive germ layers of the avian embryo proper, extraembryonic membranes begin to form that will function to support the developing embryo. As shown in FIG. 2, these include the splanchnopleure that will form the yolk sac, the somatopleure, that will form the amnion and the chorion, and the allantoic membrane, that will eventually fuse with the chorion to form the chorioallantoic membrane. These membranes become vascularized and provide the developing embryo with nutrients from the yolk sac and gas exchange across the egg shell.

In contrast to avian species, mammalian development is viviparous and often occurs in the context of the uterus, where embryonic membranes form analogous to that in the avian egg, but the extraction of nutrition from the maternal circulation can occur either through either the chorion, the allantoic membrane, or the yolk sac membrane depending on the mammalian species. Generally speaking, in most mammals, the yolk sac provides little if any nutritional support.

The avian egg provides an unusually promising environment for the cultivation of human cells. As described herein, novel means of culturing and maintaining hES cells, hED cells, and cells differentiated from such cells are described utilizing telolecithal or eutelolecithal eggs or cells derived from embryonated telolecithal or eutelolecithal eggs. In addition, it is possible to utilize telolecithal or eutelolecithal eggs to support the in ovo development on non-human mammalian embryos and fetuses and to reconstitute embryonic stem cells and embryo-derived cells from chromatin from mammalian species.

SUMMARY OF THE INVENTION

The present invention provides methods for the culture of animal pluripotent stem cells and their differentiated progeny cells, tissues, and organs, and nonhuman animal embryos and fetuses.

More specifically, this invention provides a novel method of culturing embryos, fetuses, cells, tissues, and organs in ovo in telolecithal or eutelolecithal eggs and for the culture of hES cells, hED cells, and cells differentiated from such cells in co-culture with cells derived from embryonated telolecithal or eutelolecithal eggs for numerous commercial applications that improves yield, efficiency, cost, and risk in each of the above categories.

In one aspect of the invention, the method comprises: the utilization of an unfertilized telolecithal or eutelolecithal egg of the avian or egg-laying mammal species as a culture system for the growth and differentiation of mammalian stem cells.

In another aspect of the invention, stem cells are implanted within the vitelline membranes of the telolecithal or eutelolecithal oocyte and subsequently incubated to allow the differentiation of mammalian extraembryonic membranes whereby a mammalian yolk sac splanchnospleuric membrane surrounds the avian yolk.

In still another aspect of the invention, mammalian embryonic cells can be injected in ovo in juxtaposition to the vitelline membrane and incubated over time to allow the formation of a plurality of mammalian extraembryonic membranes in the avian egg, including the formation of mammalian splanchopleure, somatopleure, chorionic membrane (CAM), allantoic membrane, amniotic membrane, or yolk sac membranes. The generation of such extraembryonic membranes has great utility in supporting the differentiation of hES or hED cells for purposes of research or manufacture, or, in the case of non-human mammalian species, in supporting advanced development of embryos and fetuses for research or production of agricultural animals.

In yet another aspect of the invention, mammalian embryonic cells (such as hES cells or hED cells, or cells differentiated from such cells) can be injected in ovo in juxtaposition to the vitelline membrane of an embryonated avian egg to produce differentiated cells vascularized by the vitelline vascular plexus.

In another aspect of the invention, mammalian pluripotent stem cells (such as hES cells or hED cells, or cells differentiated from such cells) are injected in juxtaposition with the CAM, or in a region of the egg in which the CAM will eventually invade. The vasculature of the CAM then supplies vascularization to the growing and differentiating mass of cells.

In still yet another aspect of the invention, mammalian pluripotent stem cells are injected in the amniotic cavity, albumin, air space, allantoic cavity, extraembryonic coelom, or the yolk sac of the egg and allowed to differentiate.

In another aspect of the invention, inducers such as factors including hormones, growth factors, extracellular matrix components, or inducer cells are introduced into the avian egg with the stem cells of the above-mentioned protocols in order to influence the course of differentiation of the injected mammalian pluripotent stem cells.

In a particular aspect of this invention, the inducer cells of the pervious embodiment include avian SPF cells from diverse differentiated cell lineages including somatic cells obtained from the differentiation of chicken embryonic stem (cES) cells.

In another aspect of the invention, whole and intact non-human embryos and fetuses can be cultured in the avian egg with or without a shell or shell membrane (in ovo) through the injection of nonhuman embryos or embryo-derived cells into the egg in juxtaposition to the vitelline membrane. Whole and intact human embryos could also be developed in ovo using the described invention, however, it is the belief of the inventors that the use of the technology for this purpose is not ethical and claims for such uses are not sought in the present invention.

In still another aspect of the present invention, intact non-human mammalian embryos and fetuses can be grown in ovo and used to induce the differentiation of injected mammalian pluripotent stem cells including hES and HEDC cells by injecting such hES, hED, or cells differentiated from such cells into chosen sites of the differentiating non-human animal embryo or fetus to induce the differentiation of such injected cells.

In another particular aspect of the invention, nonhuman mammalian embryos and fetuses can be cultivated in ovo by means of the transfer of chromatin into the blastodisc of an unfertilized avian egg, where the avian oocyte is activated and induced to undergo rounds of karyokinesis and cytokinesis and subsequent development. Human chromatin can also be introduced into the blastodisc of the avian egg for the purpose of reconstituting intact embryonic cells from reprogrammed chromatin, but the development of intact human embryos post gastrulation and fetuses by this means is considered unethical and claims relating to human post-gastrulation embryos or fetuses cultured in ovo are not sought in this application.

In another aspect of the invention, embryonic cells from SPF species including SPF embryonic chicken cells are used as feeder cells for the in vitro cultivation of mammalian ES cells including hES and hEDC cells in vitro or in ovo.

In another aspect of the invention, somatic cells from SPF species including SPF embryonic chicken cells are used as cells to induce the differentiation of hES or hED cells or cells differentiated from such cells. The SPF inducer cells may be viable or mitotically inactivated by radiation or chemical treatment, and may be co-cultured with the human stem cells in a variety of culture conditions including in vitro and in ovo co-culture.

Other features and advantages of the invention will be apparent from the following description and from the claims.

DETAILED DESCRIPTION OF THE INVENTION

Figure 1:
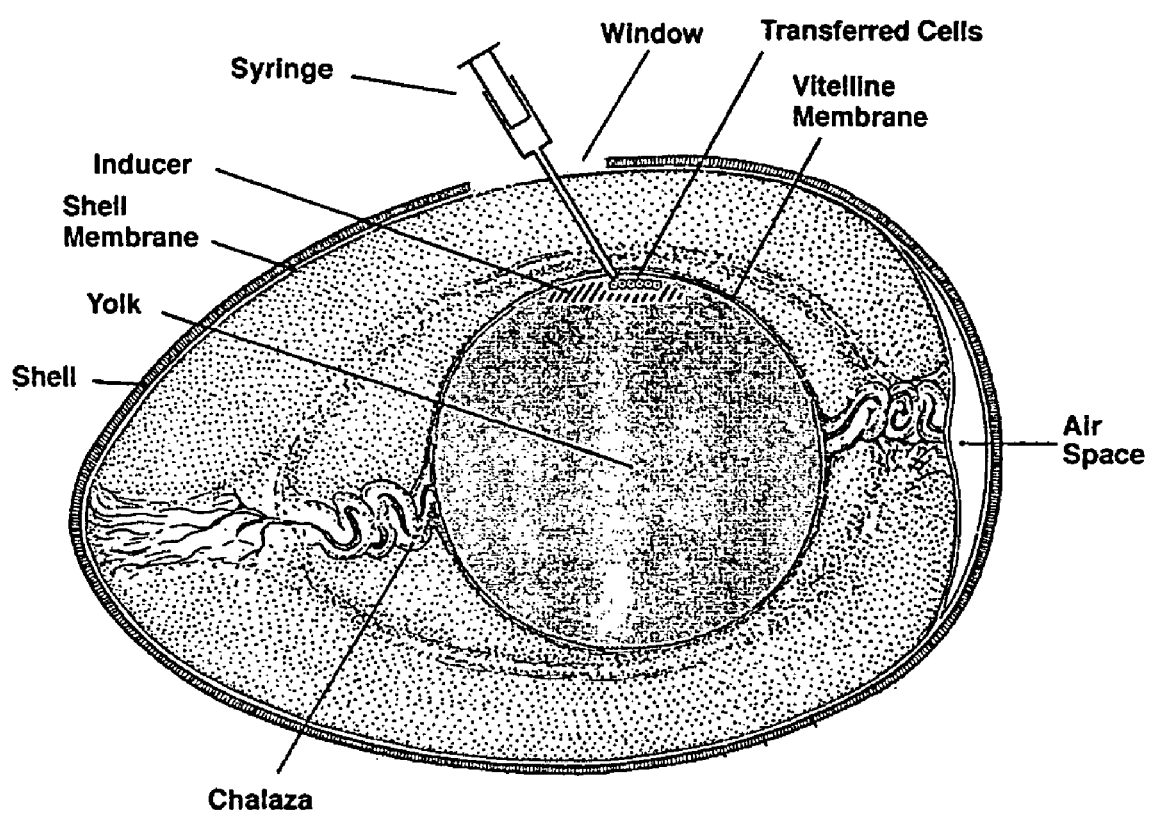
FIG. 1 is a drawing illustrating the transfer of stem cells in juxtaposition to the vitelline membrane of the unfertilized or early embryonated avian egg. In the example shown, the cells are injected with an inducer to influence the course of differentiation of the stem cells.

Table of Abbreviations $[Ca^{+2}]i$—Intracellular calcium concentration
CAM—Chorioallantoic membrane
CEF—Chick Embryo Fibroblast
cES Cell—Chicken embryonic stem cell
ES Cell—Embryonic stem cells derived from a morula or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell.
HEDC—Human Embryo-Derived Cells
hES Cell—Human embryonic stem cells
ICM—Inner Cell Mass of the blastocyst embryo.
ICSI—Intracytoplasmic sperm injection
MII—Metaphase II
NT—Nuclear Transfer
SPF—Specific Pathogen-Free The present invention provides methods for the culture of mammalian stem cells, differentiated progeny cells, tissues and organs, and non-human mammalian embryos and fetuses in a telolecithal or eutelolecithal egg such as that of avian or egg laying mammalian species (in ovo). The term "in ovo" refers to residence within a shelled telolecithal or eutelolecithal egg, or in the presence of the components of such an egg or eggs cultured in a container other than an egg shell, such container being composed of polymers, glass, or metal. The telolecithal or eutelolecithal eggs useful in the present invention may be from the common domestic chicken (*Gallus gallus domesticus*) or from any other avian species including but not limited to the turkey (*Meleagris*), quail (*Coturnix*), and duck (*Anas*) or an egg-laying mammals such as those of the Order Monotremata. The avian eggs useful in this invention for the production of therapeutic products include specific pathogen-free (SPF) eggs. The term "specific pathogen-free" refers to eggs that have been obtained from animals reared in conditions to insure that the animals and their eggs are free of known pathogens including avian pathogenic viruses.

The term "suicide gene" refers to genes that may be introduced into the mammalian stem cells or into the avian inducer cells or into the avian system providing vascular support, such that upon stimulation, the cells that carry the suicide gene can be induced to die. Such suicide genes are well known in the art and include the use of herpes simplex virus thymidine kinase that in the presence of gancyclovir can cause the death of the cell carrying the gene. The term "mitotically inactivated" refers to cells that have been rendered incapable of subsequent cell division by the exposure of such cells to agents that damage the DNA of such cells such that the cells undergo DNA damage checkpoint arrest or apoptosis. Such mitotic inactivation can be achieved by techniques well known in the art such as the use of exogenous radiation, or chemical agents including mitomycin C.

The term "teratoma" refers to a benign mass of cells differentiating from pluripotent stem cells that organize into complex tissues in three dimensions, though lacking the normal and intact form of an animal and incapable of independent life. By way of example, teratomas have been reported to occur following the injection of hES cells into the skeletal muscle or peritoneum of immunocompromised mice where such teratomas contain intenstine, skin, teeth, renal tissue, neuronal tissue, bone, cartilage, and so on.

The term "chorioallantoic membrane" or "CAM" refers to the outermost extraembryonic membrane that eventually lines the noncellular eggshell membrane. The CAM is formed by the fusion of the splanchnic mesoderm of the allantois and the somatic mesoderm of the chorion. The fused doublet of allanois and chorion will cover the entire inner surface of the egg shell by day 12.

The term "pluripotent stem cells" refers to animal cells capable of differentiating into more than one differentiated cell type. Such cells include hES cells, hEDCs, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "embryonic stem cells" (ES cells) refers to cells derived from the inner cell mass of blastocysts or morulae that have been serially passaged as cell lines. The ES cells may be derived from fertilization of an egg cell with sperm or DNA, nuclear transfer, parthenogenesis, or by means to generate hES cells with homozygosity in the MHC region. The term "human embryonic stem cells" (hES cells) refers to cells derived from the inner cell mass of human blastocysts or morulae that have been serially passaged as cell lines. The hES cells may be derived from fertilization of an egg cell with sperm or DNA, nuclear transfer, parthenogenesis, or by means to generate hES cells with homozygosity in the HLA region.

The term "human embryo-derived cells" (HEDC) refer to morula-derived cells, blastocyst-derived cells including those of the inner cell mass, embryonic shield, or epiblast, or other totipotent or pluripotent stem cells of the early embryo, including primitive endoderm, ectoderm, and mesoderm and their derivatives, but excluding hES cells that have been passaged as cell lines. The hEDC cells may be derived from fertilization of an egg cell with sperm or DNA, nuclear transfer, parthenogenesis, or by means to generate hES cells with homozygosity in the HLA region.

In one embodiment of the invention, mammalian pluripotent stem cells with or without inducer molecules or cells are injected within and in juxtaposition to the vitelline membranes of the unembryonated egg (FIG. 1). One mammalian pluripotent cell, or a plurality of cells, for example, a colony of cultured mammalian pluripotent stem cells such as ES cells, in particular hES or HEDC cells, can be injected by techniques well known in the art, such as incubating an egg at 37-39° C. in 60% humidity, the shell cleaned with 70% ethanol, and using a sterile syringe, approximately 2.5 mL of albumin will be removed. This allows a small, typically 1.5 cm$^2$ window in the shell to be made and cells to be injected with a glass pipette, and subsequent covering the windowed portion of the shell with a sealant such as common kitchen wrap and subsequent culture at 37° C. with or without supplemental calcium and ascorbate to approximate the physiological levels of the corresponding mammalian species in a standard tissue culture incubator. The egg may be injected at one site, or multiple sites, including at or near the blastodisc, depending on the nature of the cells and the type of product desired.

In addition, the cells with or without inducer may be injected within the vitelline membrane but external to the developing embryo of an embryonated egg such that the differentiated cells are vascularized by the vitelline vascular plexus. The differentiated cells can then be removed from the egg and purified from the yolk sac prior to hatching. Alternatively, the chicken can be allowed to develop to hatching, in which case the yolk sac membrane is absorbed within the body cavity of the chick and the mammalian teratoma continues to develop within the body of the hatched chick and the differentiated mammalian cells can be removed post hatch. Some of the advantages of obtaining the cells post hatch are that it allows more time for greater growth and development of the teratoma and it provides early exposure of the chick to the mammalian pluripotent stem cells which tolerizes the immune system and lessens chances of rejection. As in the case of injection of cells into unembryonated eggs, the injection of the cells into embryonated eggs is by techniques well known in the art for the injection of cells, such as the injection of avian blastodermal cells into the blastoderm of a fertilized egg to generate chimeras. The egg is cultured at 37° C. or in the proximity to the normal temperature for human cells (i.e. 35-39° C.) at about 60% humidity, the shell cleaned with 70% ethanol, and using a sterile syringe, approximately 2.5 mL of albumin will be removed. This allows a small, typically 1.5 cm$^2$ window to be made in the shell for the introduction of cells with or without supplemental calcium and ascorbate to approximate the physiological levels of the corresponding mammalian species.

Figure 2:
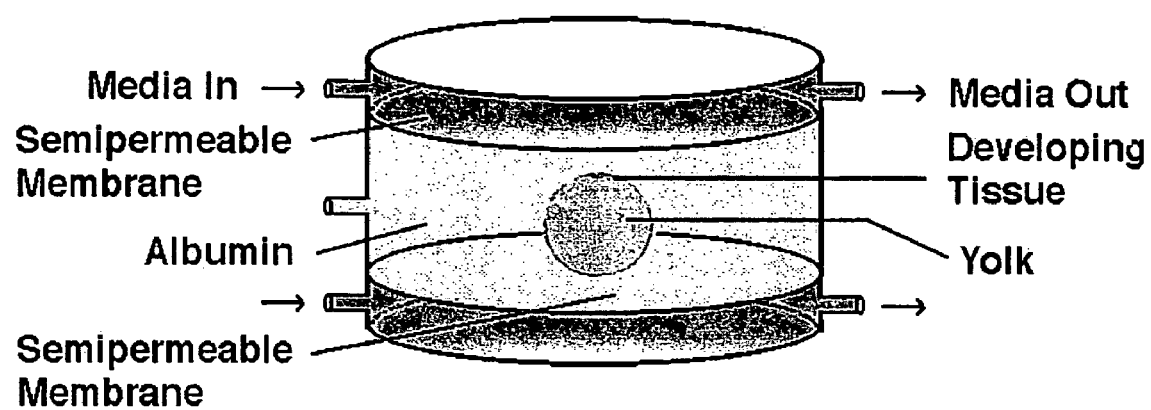
FIG. 2 is a drawing of an artificial culture vessel for maintaining mammalian pluripotent stem cells and derivative cells in the presence of components of a telolecithal or eutelolecithal egg.

In another embodiment of the invention, the components of the egg will be transferred to a container such as that shown in FIG. 2 to replace the function of the egg shell and to facilitate the manipulation of the culture system. Such container may contain a transparent component to allow the viewing of the developing tissue, ports for the removal, replacement, or addition of egg components such as egg albumin or a culture medium or matrix substrate substituting for albumin, egg yolk, mammalian pluripotent stem cells including hES or HEDC, or inducer molecules or cells, the cannulation of blood vessels within the differentiating tissue for external circulatory or respiratory support, or a system such as a semipermeable membrane to facilitate the diffusion of gases and small molecules into and out of the culture system. The use of an artificial container also allows for the introduction of egg components from multiple eggs for culture of cells of animals of long gestational age and where larger tissues or larger extraembryonic membranes are desired, with or without supplemental calcium and ascorbate to approximate the physiological levels of the corresponding mammalian species.

Figure 3:
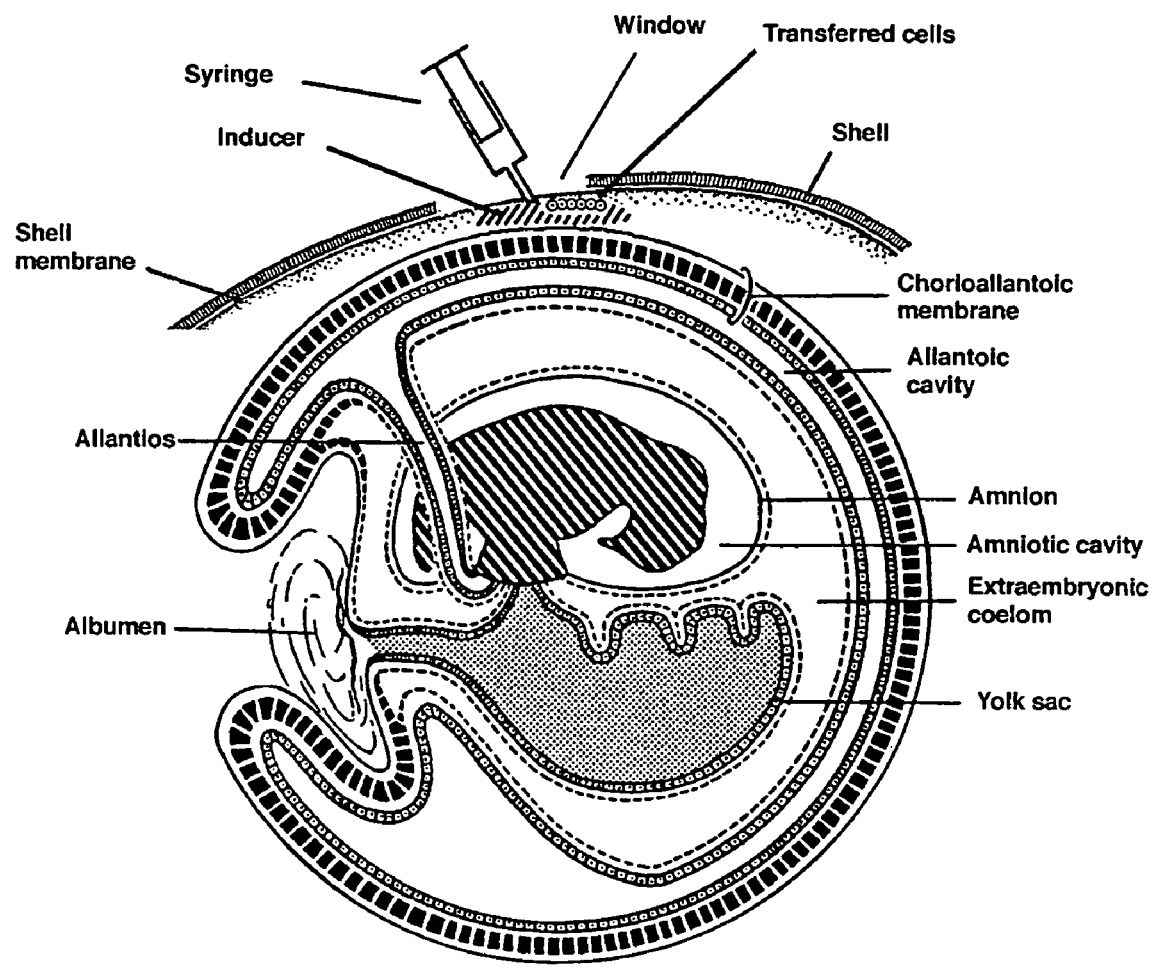
FIG. 3 is a drawing of the various anatomical structures of the fertilized chicken egg, showing the location of the chorioallantoic membrane (CAM) and the placement of mammalian pluripotent stem cells and inducer in juxtaposition to the CAM membrane.
Figure 4:
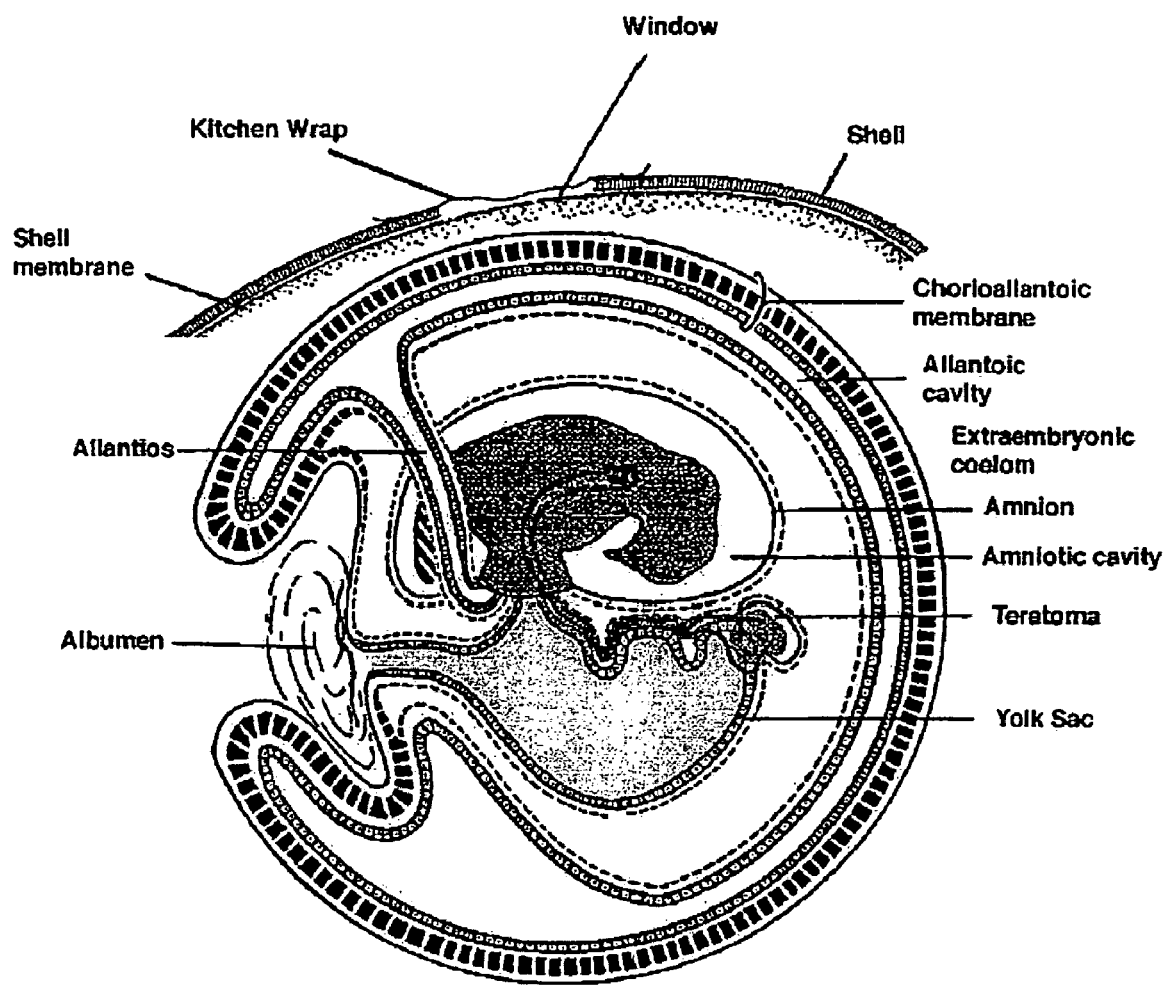
FIG. 4 is a drawing showing the result of placement of mammalian ES cells or embryo-derived cells within the vitelline membrane of an embryonated egg such that the growing teratoma is vascularized by the chick's vitelline vascular plexus.

In another embodiment of the invention, mammalian pluripotent stem cells including hES and hEDC cells are injected in the proximity of the shell membrane to form a teratoma that will subsequently become vascularized by the growing CAM membrane (FIG. 3). Typically, in the case of the chicken egg, the egg will be incubated at approximately 37° C. and 60% humidity, the shell cleaned with 70% ethanol, and using a sterile syringe, approximately 2.5 mL of albumin will be removed. This allows a small, typically 1.5 cm$^2$ window to be cut in the shell and the shell membrane allowing the mammalian pluripotent cells to be injected within the albumin and in juxtaposition to the shell membrane. The mammalian pluripotent cells may be injected between day 1 and day 17. The teratoma may subsequently be removed and cultured in organ culture with the attached vasculature used to perfuse the growing tissue with blood or tissue culture media. Any residual avian cells may be removed by activation of the avian suicide genes.

In another embodiment of the invention, mammalian pluripotent stem cells including hES and HEDC are injected by the above techniques in the amniotic cavity, albumin, air space, allantoic cavity, extraembryonic coelom, or the yolk sac of the egg and allowed to differentiate over time in the incubated egg.

In another embodiment of the invention, the inducer includes cells that are derived from cells of a heterologous species, such as chicken somatic cells inducing the differentiation of hES cells. Such cells can be cells that normally occur in juxtaposition to the cell of interest and include stromal cells and endothelial cells from the organ or parenchyma of interest. The somatic inducer cells can be obtained from a variety genotypes including SPF eggs to reduce the risk of pathogen transmission. Such eggs are commercially available (Charles River Laboratories) and are free of such pathogens as Avian Adenoviruses I-III, Avian Encephalomyelitis, Avian Influenza (Type A), Avian Nephritis Virus, Avian Paramyxovirus Type 2, Avian Reovirus, Avian Rhinotracheitis Virus, Avian Rotavirus, Avian Tuberculosis, Chicken Anemia Virus, Endogenous GS Antigen, Fowl Pox, *Hemophilus paragallinarum*, Infectious Bronchitis (Ark, Conn, JMK, and Mass), Infectious Bursal Disease, Infectious Laryngotracheitis, Lymphoid Leukosis A,B, Lymphoid Leukosis Viiruses, Marek's Disease (Serotypes 1,2,3), *Mycoplasma gallisepticum, Mycoplasma synoviae*, Newcastle Disease, Reticuloendotheliosis Virus, *Salmonella pullorum-gallinarum*, and other *Salmonella* species.

In another embodiment of the invention, the inducer cells are derived from ES cells of a heterologous species. By way of non-limiting example, the inducer cells may be cES cells differentiated into somatic cells that function in inducing the specific differentiation of hES cells. The cES cells can be obtained from a variety genotypes including SPF eggs to reduce the risk of pathogen transmission. In addition, since the cES cells can be cultured indefinitely in an undifferentiated state, they can be genetically modified using techniques well known in the art for improved performance as inducer cells. Such genetic modifications include the introduction of suicide genes that allow the destruction of the inducer cells prior to use, modified to express cell surface antigens that facilitate the removal of the inducer cells by affinity methods well known in the art, or the inducer ES cells may be modified by gene trap vectors in order to obtain ES cell clones that express markers such as fluorescent proteins that facilitate the purification and identification of particular differentiated cell types as inducer cell lines.

In another embodiment of the invention, the inducer is one of a number of extracellular signaling molecules including growth factors, cytokines, extracellular matrix components, nucleic acids encoding the foregoing, steroids, and morphogens or neutralizing antibodies to such factors. Such inducers include but are not limited to: cytokines such as interleukin-alpha A, interferon-alpha A/D, interferon-beta, interferon-gamma, interferon-gamma-inducible protein-10, interleukin-1-17, keratinocyte growth factor, leptin, leukemia inhibitory factor, macrophage colony-stimulating factor, and macrophage inflammatory protein-1 alpha, 1-beta, 2, 3 alpha, 3 beta, and monocyte chemotactic protein 1-3.

Differentiation agents according to the invention also include growth factors such as 6kine, activin A, amphiregulin, angiogenin, β-endothelial cell growth factor, β-cellulin, brain-derived neurotrophic factor, C10, cardiotrophin-1, ciliary neurotrophic factor, cytokine-induced neutrophil chemoattractant-1, eotaxin, epidermal growth factor, epithelial neutrophil activating peptide-78, erythropioetin, estrogen receptor-alpha, estrogen receptor-beta, fibroblast growth factor (acidic and basic), heparin, FLT-3/FLK-2 ligand, glial cell line-derived neurotrophic factor, Gly-His-Lys, granulocyte colony stimulating factor, granulocytomacrophage colony stimulating factor, GRO-α/MGSA, GRO-β, GRO-gamma, HCC-1, heparin-binding epidermal growth factor, hepatocyte growth factor, heregulin-alpha, insulin, insulin growth factor binding protein-1, insulin-like growth factor binding protein-1, insulin-like growth factor, insulin-like growth factor II, nerve growth factor, neurotophin-3,4, oncostatin M, placenta growth factor, pleiotrophin, rantes, stem cell factor, stromal cell-derived factor 1B, thrombopoietin, transforming growth factor-(alpha, beta1,2,3,4,5), tumor necrosis factor (alpha and beta), vascular endothelial growth factors, and bone morphogenic proteins.

Differentiation agents according to the invention also include hormones and hormone antagonists such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagons, gonadotropin, L-3,3',5'-triiodothyronine, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxin-binding globulin, and vasopressin.

In addition, differentiation agents according to the invention include extracellular matrix components such as fibronectin, proteolytic fragments of fibronectin, laminin, tenascin, thrombospondin, and proteoglycans such as aggrecan, heparan sulphate proteoglycan, chontroitin sulphate proteoglycan, and syndecan. Such extracellular matrix components may be injected at or near the site of the injected pluripotent stem cells in a soluble form or attached to an immobilized matrix such as a tissue membrane or a membrane made of a synthetic polymer.

Differentiation agents according to the invention also include antibodies to the previously-mentioned cytokines, growth factors, hormones, and extracellular matrix components, and their receptors.

The present invention also provides for a means of developing human extra-embryonic membranes that can function to support the near normal differentiation of cells from hES cells or hED cells in ovo. The injection of such human pluripotent stem cells such as hES cells at or near the vitelline membrane of either an embryonated or unembryonated egg by injection and subsequent incubation techniques well known in the art and described in application above, results in the differentiation of some of the injected cells into extra-embryonic membranes such as human amnion, chorion, and yolk sac, that in turn provide laboratory models of cell differentiation, and the derivation of yolk sac hematopoietic precursor cells, and extra-embryonic membranes useful in supporting the growth and differentiation of such stem cells.

The present invention also provides for a means of developing mammalian extra-embryonic membranes that can function to support the near normal development of non-human fetuses. In particular, such species as the domestic pig display extra-embryonic membrane formation closely resembling that of avian species and such animals can be gestated within the avian egg or within an artificial device such as that shown in FIG. 2. The inner cell mass or embryonic disc or embryonic stem cells of such non-human mammalian preimplantation embryo or peri-implantation embryo can be grafted into or near the blastodisc of an unfertilized avian egg, or the blastoderm of a fertilized avian egg can be removed or inactivated and replaced by the intact ICM or embryonic disc of a non-human mammalian embryo with or without supplemental calcium and ascorbate to approximate the physiological levels of the corresponding mammalian species The present invention also provides a means of influencing the differentiated state of cultured hES cells, hED cells, and cells differentiated from such cells by co-culturing such cells with SPF avian differentiated cells. SPF avian chick embryo fibroblasts, including but not limited to chick embryo fibroblasts from SPF embryonated eggs at nine days of culture may be isolated by techniques well known in the art such as by removing such nine day-old chick embryos, disaggregating the tissues, and plating the cells in standard fibroblast growth conditions such as MEM medium supplemented with 10% FBS or defined pathogen-free medium. hES cells may then be serially passaged on mitotically-inactivated SPF chick embryo fibroblasts instead of using feeder cells such as murine embryo fibroblasts with an uncharacterized pathogen status. The co-culture of hES cells with SPF chick embryo fibroblasts has a clear utility in facilitating the scale up of hES cells in pathogen-free culture conditions. The use of other specific SPF chick cells may similarly be used where such cells are known to cause the induction of differentiation in order to influence the differentiation of hES, hED cells, or other downstream pluripotent human cells. Examples of cell types that function as inducers of differentiation are well known in the art and include mesodermal cells such as the stromal cells from the aorta-gonadal-mesonephros region which induce definitive hematopoiesis in pluripotent stem cells, ectodermal cells such as the optic vesicle cells, or mesenchymal cells from the optic vesicle that induce the differentiation of ectodermal cells into lens cells, and endodermal cells such as the induction of pancreatic islet cells, including pancreatic beta cells from primitive endodermal epithelium by pancreatic mesenchymal cells. Induction can also occur by epithelio-stromal interactions and by the use of one germ-layer to induce cells of another germ-layer, such as the use of dermal mesoderm cells to induce epidermal differentiation such as hair differentiation, mesodermally-derived cells that induce gut and ultimately pancreatic islet cell differentiation, the mesodermal cells of the ureteric bud that induce kidney differentiation, the mesodermal induction of epithelium to produce pharyngeal thymus and thyroid differentiation, liver mesenchymal cells that induce primitive epithelium to differentiate into hepatic cords and liver parenchyma, gut mesenchymal cells that induce primitive epithelial cells to differentiate into gut, tracheal mesenchymal cells that induce respiratory differentiation such as respiratory epithelium, Such inducer cells can be removed from the corresponding region of an SPF chick embryo by standard dissection, or isolated from SPF chick ES cell lines utilizing genetic markers for that lineage of cells, such as exogenous markers with exogenous promoters or using the endogenous promoter and gene trap technology.

The present invention also provides a means of reconstituting mammalian cells from chromatin, by removing or inactivating the avian DNA from the blastodisc of an avian embryo using techniques well known in the art, and replacing said genome with the haploid or preferably the diploid genome of a mammalian cell. The mammalian cell genome may be by way of example, human somatic cell-derived chromatin that has been reprogrammed and condensed by exposure in vitro to extracts or purified components from metaphase II oocytes as is known in the art. Subsequent or at about the time of the transfer of chromatin, the oocyte is activated such that there is an elevation of intracellular calcium. Current strategies for the activation of the oocyte in the absence of sperm, commonly known as parthenogenetic activation are well known in the art, and include chemical activation to elevate intracellular calcium concentration followed by the down-regulation of maturation-promoting factor (MPF), the injection of sperm extracts or purified sperm factor, or incubation in strontium chloride. In addition, this invention provides a novel method of activating the oocyte of a telolecithal or eutelolecithal egg in conjunction with the transfer of chromatin from a mammalian species, said method being the injection and subsequent removal of a sperm, multiple sperm, or sperm heads, and their subsequent removal. As a result of chromatin transfer and activation, rounds of karyokinesis and cytokinesis that follow result in cells similar in nature to hES or HEDC cells on the in juxtaposition to the vitelline membrane as previously described.

Applications

It is envisioned that the disclosed methods for the culture of animal tissues are generally useful in mammalian subjects, including human and non-human subjects, and particularly in the culture of non-human embryos and fetuses and for the culture and differentiation of mammalian pluripotent stem cells, in particular, hES cells and HEDC.

Following a review of the present disclosure, one skilled in the art of stem cell culture and the manipulation of telolecithal eggs such as avian eggs, can readily implement the invention in the culture of non-human mammalian embryos and fetuses, and in the culture of mammalian stem cells including human stem cells. As described further herein below, the methods of the present invention can be used for culturing non-human embryos such as pigs to advanced stages of development, and for the manufacture of animal cells, such as human cells useful in drug discovery, basic research, and in cell therapy.

A. Development of Mammalian Cells and Tissues in the Avian Egg

In one embodiment of the invention, hES cells and other mammalian ES cells are cultured and differentiated within the avian egg. The term "avian egg" refers to the fertilized or unfertilized egg of an avian species including but not limited to eggs of the domestic chicken (*Gallus domesticus*), the turkey, duck, ostrich, and quail. However, complex tissues can be produced using this invention, similar to the production of teratomas which are disorganized aggregations of human tissue that form after the injection of human embryonic stem cells into immunocompromised mice.

The resultant differentiated progenitor cells or fully differentiated cells of the present invention, preferably human differentiated cells, have numerous therapeutic and diagnostic, and basic research applications. Most specifically, such differentiated cells may be used for cell transplantation therapies. Human differentiated cells have application in the treatment of numerous disease conditions.

The subject differentiated cells may be used to obtain any desired differentiated cell type. Therapeutic useages of such differentiated cells are unparalleled. For example, human hematopoietic stem cells and hemangioblasts may be used to treat many diseases that compromise the immune system, such as AIDS, cancer therapy, or age-related immune dysfunction. Hematopoietic stem cells can be obtained, e.g., by fusing adult somatic cells of a cancer or AIDS patient, e.g., fibroblasts or blood cells with an enucleated oocyte, obtaining inner cell mass cells, and culturing such cells in ovo under conditions which favor differentiation until hematopoietic stem cells or hemangioblasts are obtained. By way of a non-limiting example, hES or HEDC cells or primitive mesodermal cells derived from such cells can be injected in ovo using one of the techniques described herein in conjunction with stromal fibroblasts from the aorta-gonadal-mesonephros region of a non-human mammalian embryo or fetus or avian species to induce the differentiation of the cells into hemangioblasts and hematopoietic stem cells. Such cells may then be used with or without genetic modification for the treatment of diseases including AIDS, cancer, and immune dysfunction. The cells can also be used in veterinary practice to treat canine or feline disease using cell therapy.

Alternatively, adult somatic cells from a patient with a neurological disorder may be fused with an enucleated oocyte, human inner cell mass cells obtained therefrom, and such cells cultured in ovo under differentiation conditions to produce neural cell lines and neural progenitor cells lines. Specific diseases treatable by transplantation of such human neural cells include, by way of example, Parkinson's disease, Alzheimer's disease, ALS, palsy, and spinal cord injury among others. In the specific case of Parkinson's disease, it has been demonstrated that transplanted fetal brain neural cells make the proper synapses with surrounding cells and produce dopamine. This can result in long-term reversal of Parkinson's disease symptoms and disease progression.

The great advantage of the subject invention is that it provides an essentially limitless supply of isogenic or homozygous MHC cells suitable for transplantation. Therefore, it will obviate the significant problem associated with current transplantation methods, i.e., rejection of the transplanted tissue which may occur because of host-vs-graft or graft-vs-host rejection. Conventionally, rejection is prevented or reduced by the administration or anti-rejection drugs such as cyclosponine. However, such drugs have significant adverse side-effects, e.g., immunosuppression, carcinogenic properties, as well as being costly. The present invention will eliminate, or in the case of homozygous MHC cells, greatly reduce the need for anti-rejection drugs.

In addition, the present invention provides a means of directly differentiating cells in the context of a SPF culture system capable of generating complex tissues. It also allows for the introduction of inducer molecules and cells from similar or identical SPF species to direct the differentiation of the cells without the complication of pathogen transmission from murine or other retroviruses or other unknown agents.

In addition, the present invention provides methods to culture mammalian teratomas near the CAM of an embryonated telolecithal or eutelolecithal egg such that the teratoma is provided vascular support from the developing chick. Such a teratoma can be later removed from the egg and cannulated to provide a growing and vascularized three-dimensional tissue. Since many complex tissues are limited by the rate of diffusion of gases such as oxygen and carbon dioxide and the exchange of nutrients and waste products, the ability to assemble three dimensional aggregates of cells derived from such cells as hES and HEDC cells with vasculature is an important and novel advance facilitating the production of such tissues as renal tissue, heart tissue, liver tissue, pancreatic tissue, lung, as well as many other tissue types with dimensions in excess of 0.5 mm in diameter.

B. The Transfer and Development of Non-Human Mammalian Embryos In Ovo

In another embodiment of the invention, whole and intact non-human mammalian embryos and fetuses are gestated in ovo. This system would have great utility in producing cloned offspring where the relative inefficiencies and high cost of recipient animals leads to a high end cost of product. Animals such as domestic pigs whose extraembryonic membranes closely resemble that of the avian embryo and whose placenta does not form a syncitia with the maternal uterus are especially suited for development in ovo. In addition to providing a means of gestating domestic animals, genetically modified non-human animals developed in ovo provide a sterile and SPF system for producing cells and tissues for xenotransplantation. In addition, the non-human animal developing in ovo can be used as an intact animal to induce the differentiation of mammalian pluripotent stem cells including hES and HEDC cells. By way of non-limiting example, hES or HEDC cells or primitive mesodermal cells derived from such cells can be injected into the aorta-gonadal-mesonephros region of a non-human mammalian embryo or fetus to induce the differentiation of the cells into hemangioblasts and hematopoietic stem cells.

C. The Transfer of Reprogrammed Bovine Chromatin Into the Blastodisc In Ovo

The high value placed on mature human oocytes will lead to improved technologies to remodel the chromatin of human cells in oocyte extracts, or eventually to reprogram human DNA using defined molecular components. Such technology is currently known in the art where the extract is obtained from metaphase II oocytes. The reprogrammed chromatin resulting from such reprogramming can be injected into the blastodisc of an unfertilized telolecithal or eutelolecithal egg with resulting rounds of karyokinesis and cytokinesis resulting in reconstituted and reprogrammed cells within the vitelline membrane. Such cellular reconstitution, especially where such cells can be subsequently grown and differentiated in ovo as described in the present invention, provides an efficient and cost-effective means of producing differentiated cells of many kinds under SPF conditions and would therefore have great utility and value in producing human and non-human animal cells for basic research, drug discovery, and cell therapy.

D. The Co-Culture of SPF Avian Cells and Human Pluripotent Stem Cells In Vitro

The present difficulties of differentiating human pluripotent stem cells, such as hES cells into desired differentiated cell types such as definitive hemangioblasts, pancreatic islet cells, heart muscle precursor cells, neural progenitor cells, renal cells, liver cells, lung cells, cartilage cells, or dermal cells demonstrates the need for new technologies to direct the differentiation of such pluripotent cells and to grow the cells in a defined pathogen-free culture system. In addition to providing new pathogen-free differentiation conditions, the present invention provides a novel mean of expanding hES cells in vitro with feeder cells that, unlike murine embryo fibroblasts, are known to be pathogen free, thereby allowing the hES cells to be cultured in conditions that assure their being free of exogenous pathogens and therefore minimizing the risk of transmitting pathogens to patients in need of such cell therapy.

EXAMPLES

Example 1

Figure 5:
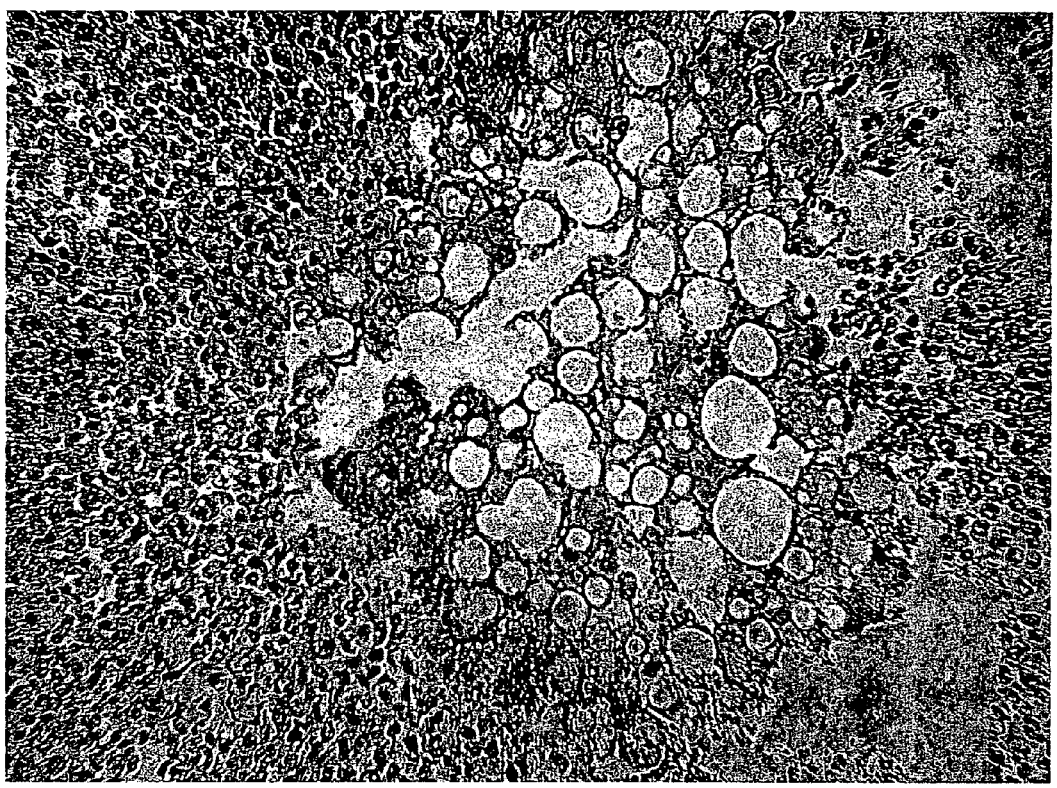
FIG. 5 shows an hematoxylin-and-eosin stained tissue section from a human teratoma formed by the placement of human ES cells within the vitelline membrane of an embryonated egg.

Human Embryo-Derived Cells Differentiated in Juxtaposition to an Embryonated Telolecithal Egg Approximately $10 \times 10^6$ human ES cells were trypsinized from culture, the trypsin was neutralized with 10% FCS in DMEM and the cells pelleted and resuspended in DMEM. Approximately $1 \times 10^6$ human ES cells were injected within the vitelline membrane of an embryonated SPF egg (Charles River) at two days of incubation at 0.5 cm from the avian embryo. At day 15, the mass of cells were identified beneath the yolk sac membrane, fixed, and Hematoxylin-and-eosin stained. In this example the cells were fixed with formaldehyde, however there are many fixative agents known to those skilled in the art which could be used. As shown in FIG. 5, dense sheets of cells ranging from vacuolated mesenchymal to round cells were visible, consistent with a predisposition to teratoma formation. Yolk sac associated epithelial cells were also observed.

Example 2

Human Embryonic Stem Cell Lines Maintained in the Undifferentiated State Using SPF-Chick Embryonic Feeder Cells Preparation of CEF:
CEF were isolated from 7-8 day old chicken embryos with the heads left on, using the previously described techniques for isolation of mouse embryonic fibroblasts. Briefly, the embryos were eviscerated, the heads left on, digested with trypsin and plated onto gelatin coated plates in DMEM, supplemented with 10% FBS, glutamine and penicillin-streptomycin. The cells were frozen at passage one and used at passage 2 after mitotic inactivation with mitomycin C.

The hES cell lines, H9, H7 (both NIH-approved) and ACT-4 were consecutively cultured on CEF for 3-6 passages without significant changes in undifferentiated morphology or growth rate. Passages used for the experiment: H-9 & H-7: H-9 started passage 38 through passage 40, H7 started 29 and through passage 35; and ACT 4 derived here from passage 9-11 and 15-19.

Figure 6:
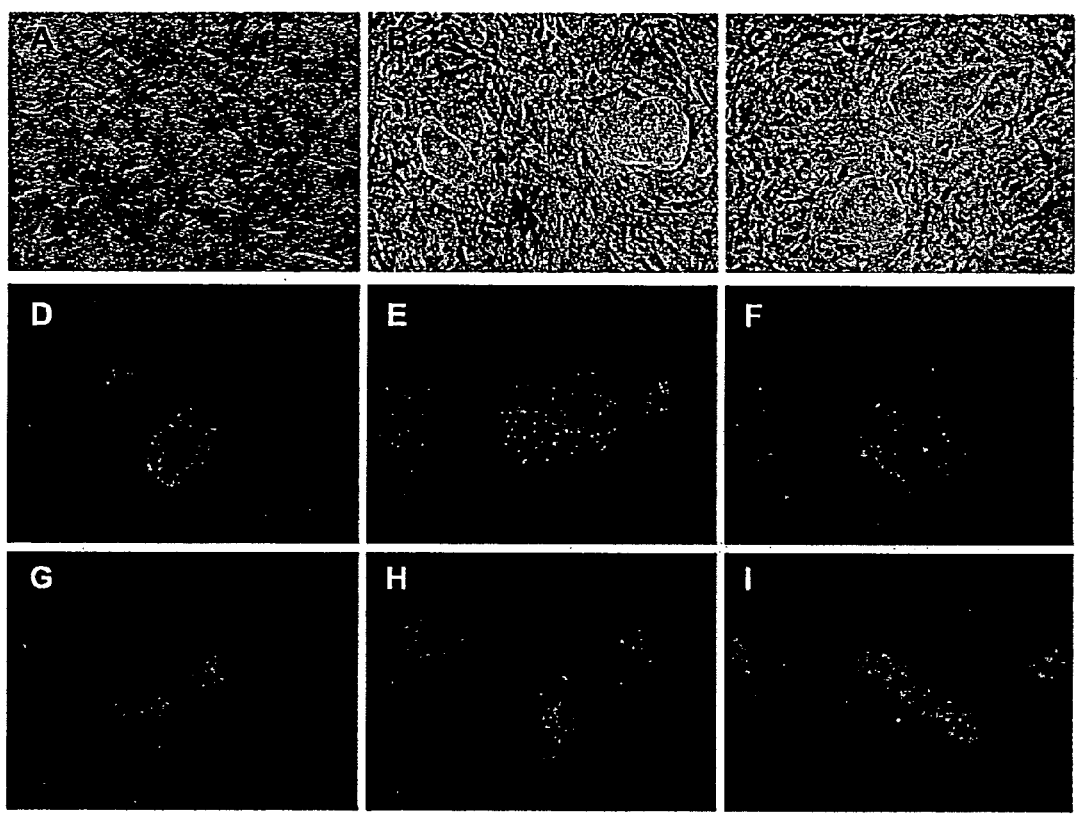
FIG. 6 shows the use of SPF chick embryo fibroblasts to stably maintain hES cell lines in an undifferentiated state. Morphology (A-C) and markers (D-I) of undifferentiated hES cells grown on CEF: A—colonies of hES cell line H9 on CEF. B, C—colonies of the hES cell line H1 grown on CEF (B) vs. on MEF (C); D-I, hES cell line H7 cultured on CEF (4 passages): D, Oct-4; E, SSEA-3; F, SSEA-4; G, alkaline phosphatase; H, TRA-1-60; I, TRA-1-81. Original magnification: A, x38; B-I, x200

Expression of the markers of pluripotency (Oct-4, alkaline phosphatase, SSEA3, SSEA-4, TRA-1-60, TRA-1-81) remained high in hES cells (line H7) after culturing on CEF for 4 consecutive passages. FIG. 6 shows the undifferentiated hES grown on the CEF.

Example 3

Non-Human Embryonic Development Within a SPF Avian Egg and the Use of the Porcine Embryo to Direct the Differentiation of Human Pluripotent Cells A cloned or normal porcine blastocyst with or without a transgenic suicide gene is held with an aspiration pipette under low magnification and the trophectoderm is torn opposite the inner cell mass to yield near-planar aggregation of cells. The torn blastocyst is injected with a 200 micron pipette into an unfertilized but fresh SPF windowed avian egg at or near the blastodisc. The resulting reconstructed egg is then resealed with kitchen wrap as is well known in the art and cultured at 37° C. on a racking platform. At the point when cell differentiation of a desired type is occurring in the porcine embryo, hES or hED cells are injected into the porcine embryo. In the case of hematopoietic differentiation, the human pluripotent stem cells are injected into the aortic-gonadal-mesonephros region of the porcine embryo to induce differentiation into hematopoietic differentiation such as hemangioblasts.

Example 4

The Use of SPF Avian Mesodermal Cells of the Aorta-Gonadal-Mesonephros Region to Direct the Differentiation of Human Pluripotent Cells into Hemangioblasts hES or hED cells are co-cultured with mesenchymal cells dissected from the aortic-gonadal-mesonephros region of SPF avian embryos to induce differentiation into hematopoietic differentiation such as hemangioblasts. The co-culture is incubated in pathogen-free tissue culture until primitive hemangioblasts are produced which are subsequently purified by the use of antigens such as CD4, AC133, c-kit, or other antigens well known in the art.

Other Embodiments

From the foregoing description, it will be apparent that variations and modifications may be made to the invention described herein to adopt it to various usages and conditions. Such embodiments are also within the scope of the following claims.

The above specification, examples, and data provide a complete description of the manufacture and use of the invention. Unless otherwise specified, all patent and non-patent references cited are hereby incorporated by reference.

We claim:

1. A method of maintaining human pluripotent stem cells in an undifferentiated state comprising co-culturing said human pluripotent stem cells with chick embryonic fibroblasts feeder cells, wherein the chick embryonic fibroblast feeder cells are obtained from an eviscerated embryo with the embryo's head left on.

2. The method of claim 1, wherein the chick embryonic fibroblasts feeder cells are specific pathogen-free.

3. The method of claim 1, wherein the human pluripotent stem cells are human embryonic stem cells.

4. The method of claim 2, wherein the human pluripotent stem cells are human embryonic stem cells.

5. The method of claim 1, wherein the chick embryonic fibroblast feeder cells are used at passage two.

6. The method of claim 2, wherein the chick embryonic fibroblast feeder cells are used at passage two.

7. A method of maintaining human pluripotent stem cells in an undifferentiated state comprising co-culturing said human pluripotent stem cells with chick embryonic fibroblasts feeder cells, wherein the chick embryonic fibroblast feeder cells are used at passage two.

8. The method of claim 7, wherein the chick embryonic fibroblasts feeder cells are specific pathogen-free.

9. The method of claim 7, wherein the human pluripotent stem cells are human embryonic stem cells.

10. The method of claim 8, wherein the human pluripotent stem cells are human embryonic stem cells.

11. A method of maintaining human pluripotent stem cells in an undifferentiated state comprising co-culturing said human pluripotent stem cells with chick embryonic fibroblasts feeder cells, wherein the chick embryonic fibroblast feeder cells were derived from a 7 or 8-day embryo.

12. The method of claim 11, wherein the chick embryonic fibroblasts feeder cells are specific pathogen-free.

13. The method of claim 11, wherein the human pluripotent stem cells are human embryonic stem cells.

14. The method of claim 12, wherein the human pluripotent stem cells are human embryonic stem cells.

* * * * *